United States Patent [19]
Tihon

[11] Patent Number: 5,738,654
[45] Date of Patent: *Apr. 14, 1998

[54] SELF CLEANSING BLADDER DRAINAGE DEVICE

[75] Inventor: Claude Tihon, Eden Prairie, Minn.

[73] Assignee: ContiMed, Inc., Eden Prairie, Minn.

[ * ] Notice: The term of this patent shall not extend beyond the expiration date of Pat. No. 5,562,622.

[21] Appl. No.: 579,592

[22] Filed: Dec. 26, 1995

Related U.S. Application Data

[63] Continuation-in-part of Ser. No. 407,297, Mar. 20, 1995, Pat. No. 5,562,622.

[51] Int. Cl.$^6$ ............................................. A61M 29/00
[52] U.S. Cl. ........................ 604/105; 604/329; 604/349; 128/761
[58] Field of Search .................. 604/54, 93, 104–107, 604/245, 349, 350, 329, 174, 177–180; 606/198, 193; 128/761, 766

[56] References Cited

U.S. PATENT DOCUMENTS

| | | | |
|---|---|---|---|
| 1,497,722 | 6/1924 | Holst-Grubbe | 604/178 |
| 2,450,217 | 9/1948 | Alcorn . | |
| 3,260,258 | 7/1966 | Berman . | |
| 3,490,456 | 1/1970 | Kortum | 604/106 |
| 3,730,187 | 5/1973 | Reynolds | 604/178 |
| 3,769,981 | 11/1973 | McWhorter . | |
| 3,774,591 | 11/1973 | Corbin | 128/761 |
| 3,811,450 | 5/1974 | Lord . | |
| 3,815,608 | 6/1974 | Spinosa | 604/105 |
| 3,821,956 | 7/1974 | Gordhammer | 604/104 |
| 4,307,723 | 12/1981 | Finney . | |
| 4,398,910 | 8/1983 | Blake | 604/93 |
| 4,501,580 | 2/1985 | Glassman . | |
| 4,645,493 | 2/1987 | Ferrando et al. | 604/174 |
| 4,666,433 | 5/1987 | Parks | 604/178 |
| 4,710,169 | 12/1987 | Christopher | 604/349 |
| 4,723,946 | 2/1988 | Kay . | |
| 4,738,667 | 4/1988 | Galloway . | |
| 5,049,140 | 9/1991 | Brenner et al. . | |
| 5,073,169 | 12/1991 | Raiken | 604/174 |
| 5,141,502 | 8/1992 | Macaluso, Jr. . | |
| 5,176,664 | 1/1993 | Weisman . | |
| 5,232,440 | 8/1993 | Wilk | 604/174 |
| 5,356,391 | 10/1994 | Stewart | 604/174 |
| 5,484,420 | 1/1996 | Russo | 604/178 |
| 5,562,622 | 10/1996 | Tihon | 604/105 |

FOREIGN PATENT DOCUMENTS

| | | |
|---|---|---|
| 326908 | 8/1989 | European Pat. Off. . |
| 4134030 | 4/1993 | Germany . |
| 2166958 | 5/1986 | United Kingdom . |

*Primary Examiner*—Mark Bockelman
*Assistant Examiner*—Chalin Smith
*Attorney, Agent, or Firm*—Haugen and Nikolai P.A.

[57] ABSTRACT

An urethral drain having deep external drainage channels, a low-profiled bladder retention segment, and a reversibly detachable collection segment, facilitates the draining of urine and fluids from the bladder. The low-profiled retention means minimizes bladder irritations and the deep external channels reduce the occurrence of infections. Incorporation of a reduced diameter smooth segment on the catheter, proximate the location of the external urethral sphincter, allows the patient to void normally and at will. Modifying the size of this smooth segment aids the function of a defective sphincter in controlling urine leakage. The drain can be worn concealed within the urethra. Flushing action from normal voiding washes out particulate matters in the urethra and the concealed drain further minimizes contamination. Together, these features improve quality of life for patients needing catheterization.

28 Claims, 12 Drawing Sheets

SELF CLEANSING BLADDER DRAINAGE DEVICE

I. CROSS REFERENCE TO RELATED APPLICATION

This application is a continuation-in-part of application Ser. No. 08/407,297, filed Mar. 20, 1995 now U.S. Pat. No. 5,562,622 and entitled "SELF-CLEANSING BLADDER DRAINAGE DEVICE".

BACKGROUND OF THE INVENTION

II. Field of the Invention

This invention relates generally to body fluid drainage devices, and more particularly to a urinary drain having improved performance characteristics.

III. Discussion of the Prior Art

Urethral catheters, such as the Foley catheter, now used for bladder drainage are essentially elongated tubular structures placed in the urethra for draining urine through the central lumen thereof. Near the distal end of the tube is an inflatable balloon which, when inflated while in the bladder, allows the catheter to be held in place. Its proximal end has a drainage port as well as a balloon inflation port. The proximal end of the catheter protrudes beyond the urethral orifice and can be attached to a bag receptacle for the collection of the near constantly dripping urine from the bladder. The collection bag is either attached to the patient's leg when the patient is ambulatory, or to the side of the bed during bed rest. At times, a plug is used in place of the bag to stop the leakage of urine from the catheter tip.

When Foley catheters or the like are used, patients are not able to void when they want to. Rather, urine is continuously drained from the bladder through the central lumen of the elongated tube and into the collection bag. Ambulatory patients are therefore obligated to have the leg bag attached to their leg, and this poses a source of great inconvenience, unsightliness and problems affecting their quality of life. Due to the fact that urine is continuously being drained from the bladder, the bladder is continuously near empty. The dome of the bladder, therefore, rests continuously on the water-filled bulging balloon retention part of the Foley catheter, causing tissue compression, irritation and erosion related adverse side effect problems. Furthermore, increased urinary tract infection is common with patients using such catheters, especially when used on a chronic basis. Though the causal factors have not been precisely identified, length of time of catheterization has been associated with an increased frequency and severity of urinary tract infection, presumably due to the migration of bacteria up the urethral tract. Frequently, yellow encrusted and mucoid proteinaceous depositions containing bacteria are found on the surfaces of the catheter with much higher concentration on the inner lumen surfaces. The mandated usage of urine receptacles causes additional associated stigma of soiled clothing, furniture and odor.

The Spinosa et al. U.S. Pat. No. 3,815,608 discloses in FIG. 9 thereof a typical Foley urinary catheter having an inflatable balloon 64 for retaining the distal end portion of the catheter with its drainage hole 56 within the urinary bladder. An alternative embodiment disclosed in FIGS. 6 and 7 of the Spinosa et al. patent depicts a urinary catheter that uses a helically threaded region thereof as the retention means in place of an inflatable balloon. This device still relies upon the central lumen 46 as the urine path while the channels 48 define between the helical threads 44 allow for "drainage of exudate discharged from the prostate gland".

SUMMARY OF THE INVENTION

The present invention provides a solution to increase the quality of life for patients who require drainage catheters by solving compression and irritation related problems, giving patients an option to carry on their daily lives more normally and reduce incidence of the common urinary tract infections. One embodiment of the invention comprises a bladder drainage device having at least one deep, open fluid-drainage channels and a low profile bladder retention means at its distal end. In addition, it can contain an essentially smooth segment, preferably narrowed, in the area of the external urethral sphincter. Urine drains from the bladder, via the open surface channels. The narrowed smooth segment permits the external urethral sphincter to function normally to shut off the leakage of urine from the bladder to the lower portion of the urethra. The drainage channels reappear below the external sphincter. When the sphincter opens, urine and fluid will flow past the relaxed sphincter area at the smooth, narrowed drain region, and down to the deep surface drainage channels below. Unlike the situation with the Foley type catheter and the catheter of FIGS. 6 and 7 of the Spinosa et al. '608 patent, where urine is continuously drained in a leaking fashion from the bladder through an internal lumen of the drainage catheter, the present configuration of the invention allows urine to be stored in the bladder until voided in mass, much as in a normal manner, when the patient is ready to do so. Due to this natural and daily multiple automatic flushing action in the urethra and channel walls by a rushing of the bolus of urine, the bladder drain of the present invention is self-cleansing without any added external pressurized flushing equipment means, such as that described in U.S. Pat. No. 4,723,946, or any added steps for the patient.

The device of the present invention, without the smooth segment, can be worn by patients in cases where constant urine drainage is required or unavoidable. Thus, the drain will have the benefits of the lower profile retention means for reduced bladder irritability, and the deep external drainage channel(s) causing urine flow to be in contact with the urethral wall to minimize colonization of bacteria and other contaminants within a lumen, thus lower possibility of infections.

The presence of the narrow, smooth segment at the site of the external urethral sphincter region allows the natural constriction of the external urethral sphincter to terminate the flow of fluid to the distal bulbous and penile urethra as the sphincter normally functions. The patient is, therefore, able to control his own voiding frequency. This permits the drain device to be worn by ambulatory patients without the necessity of an external urine drainage collection leg bag.

Patients suffering from urinary incontinence have differing degrees of contractibility of the external urinary sphincter, depending upon age and other factors. By providing a smooth surface section that can be repositioned along the length of the externally grooved drain member and which can be selected for its outer diameter, a variety of patients can be accommodated.

The distal end of the drain device located within the bladder contains a retention means for retaining it at the bladder neck. This preferably a coiled section of the flexible, deep open channeled drainage device, which is initially straightened for insertion in the urethra by a straightening stylet placed in a central lumen of the drain device. Removing the wire after drain placement restores the curl. Due to the fact that the low profile retention means is an extension of the drainage segment, no balloon is needed, nor is there a necessity for a perpendicular, upward-protruding tubing with lateral openings for the passage of urine. The retention means is spaced apart from the smooth narrowed section a distance to assure drainage within the prostatic urethra. Before exiting the urethra, the deep channels are replaced by a traditional tubular structure, the collection segment, which proceeds to exit the urethra. This collection segment collects fluid from the deep external channel(s) above, transports it beyond the meatus of the penis, and permits the attachment of a urine drainage collection bag or a plug at the proximal end. The tubular collection segment can be detached from the channeled main drain body, thus leaving the entire drain device concealed inside the urethra. This further insures minimal infection from outside contamination, and avoids the aesthetically displeasing and uncomfortable presence of an external device.

Given the anatomical differences between the urinary systems in males and females, and in particular the short length and shape configuration of the female urethra, the drainage device for a female patient preferably comprises a soft, flexible, plastic body member having a flat coil bladder retention means at its distal end and a corresponding retention means at its proximal end to prevent the device from migrating upward into the bladder. The proximal retention device is configured to conform to the vestibule proximate the urethral opening. It is preferably an open structure or perforated to permit exposure of the underlying tissue to air.

In addressing female stress incontinence, a cuff member of a chosen size appropriate for the patient may be placed about the drain member to cooperate with the urinary sphincter, allowing the sphincter to create an improved seal against the cuff to block urine flow.

Thus, the object of this invention is to greatly increase the quality of life for patients who require bladder drainage catheters.

BRIEF DESCRIPTION OF THE DRAWINGS

The foregoing features and advantages of the invention will become apparent to those skilled in the art from the following detailed description of the present invention, in which numerals in the several view refer to corresponding parts.

FIGS. 1(a) is a partial view of the bladder drain of FIG. 1, but with an alternative anchoring structure;

FIG. 9(a) is an exploded, partial, sectional view of a drain member having straight (non-spiral) surface grooves and a collection tube used therewith;

DETAILED DESCRIPTION OF THE PREFERRED EMBODIMENT

Figure 1:
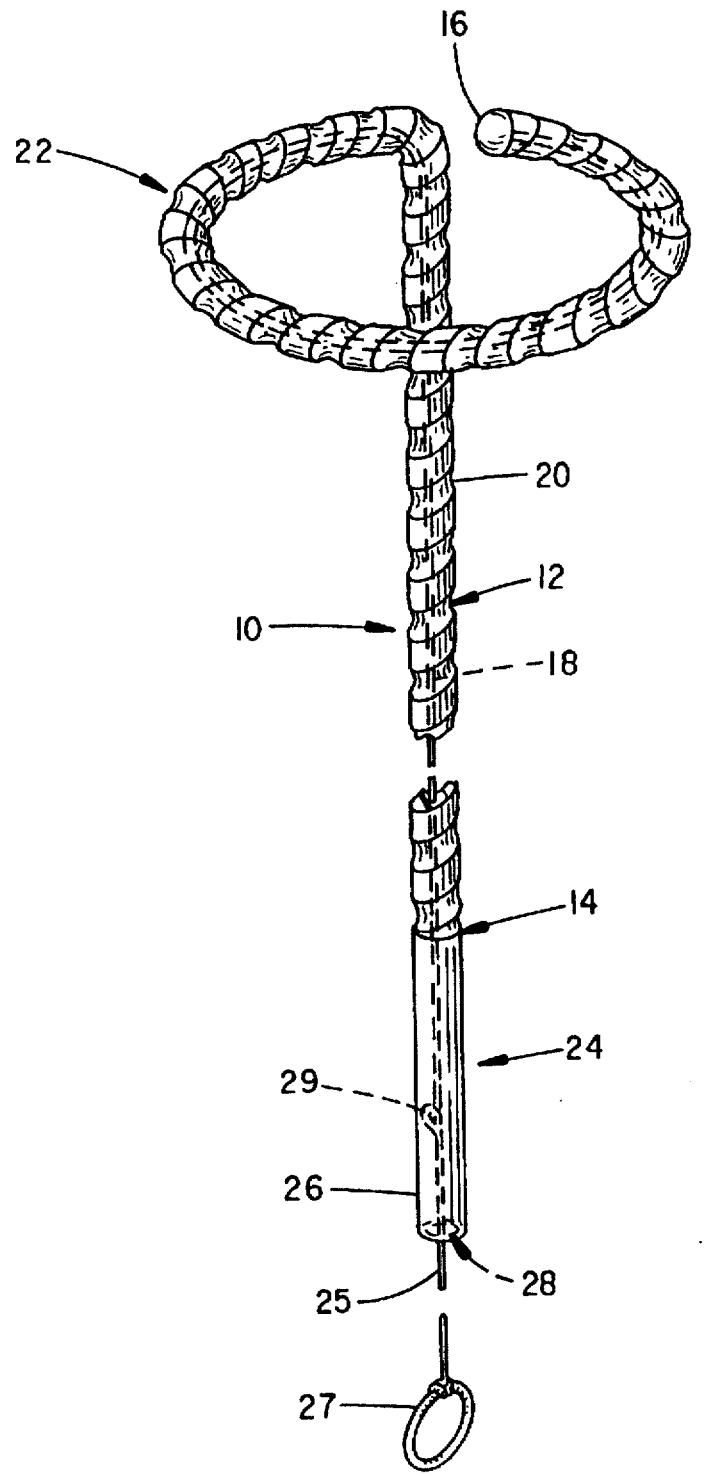
FIGS. 1 is an elevational view of a bladder drain in accordance with a first embodiment of the invention.
Figure 1:
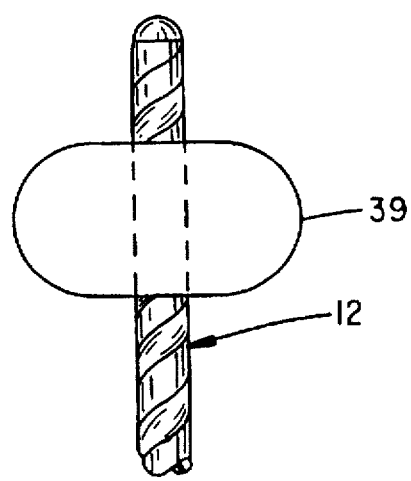

Referring first to FIG. 1, there is shown a perspective view of a bladder drainage device in accordance with a first embodiment of the invention. It is indicated generally by numeral 10 and is seen to comprise an elongated, flexible tubular member 12 having a proximal end 14 and a distal end 16 and with a styler receiving lumen 18 extending longitudinally toward but just short of the distal end 16. Thus, the distal end 16 covers the stylet lumen precluding the flow of body fluids therethrough when the drainage device 10 of the present invention is in place within the urethra of a patient.

With continued reference to FIG. 1, the body member 12 of the drainage device 10 is shown as including at least one channel 20 formed in the surface thereof and it extends substantially the entire distance from the proximal end 14 to the distal end 16. In FIG. 1, the channel 20 is shown as spirally traversing the drain body 12, but it is to be understood that the channel or channels may be straight, as well. With no limitation intended, for a drain device having an outside dimension of 0.21 inches, the helical channel 20 may have a depth of approximately 0.06 inches. The body member is preferably fabricated from a flexible polymer material, such as silicone, silastic, polyurethane or another thermoplastic elastomer having a durometer shore hardness between about 30 and 95 shore A.

Disposed proximate the distal end of the bladder drain device is a bladder retention segment 22 which comprises a curled end portion which can be straightened by the full insertion of a wire stylet (not shown) through the lumen 18. However, when the styler is fully withdrawn following insertion of the drain assembly as shown in FIG. 1 into the urethra with the distal portion within the bladder, the memory property of the plastic comprising the distal end portion of the drainage device 10 allows the preformed distal end, bladder-retaining portion 22, to form a loop or curl as illustrated. Those skilled in the art can appreciate that means other than a controlled memory property are available for creating the curl on the distal end of the drainage device. For example, a short wire segment having a preformed shaped can be embedded into the body of the drain to enhance the formation of the curl upon extraction of the styler.

Attached to the proximal end of the bladder drain 10 is a fluid collection segment, indicated generally by numeral 24.

The fluid collection segment 24 may be attached and detached from the drainage segment 12 in a manner that will be described later herein. In its simplest form, the collection segment 24 comprises an elongated plastic tube having an internal lumen extending from the proximal end 14 of the drain segment 10 to an open distal end 28 which forms the drain outlet. The collection segment 24 can accept a drainage bag or a plug not shown.

To facilitate removal of the drain, a strand such as a monofilament nylon line 25, is fixedly secured to the proximal end 14 of the drain 12 and extends beyond the proximal end 28 of the collection segment 24 and out the urethral opening in the penis. By grasping the monofilament line 25 by the loop 27 and pulling on the line, the memory property of the fixation member 22 is overcome and the drain can be readily pulled through the urethra and out the end of the penis. If desired, the line 25 may terminate short of the proximal end 28 of the collection segment 24 and in that event, an instrument having a hook on it may be passed up the lumen of the collection segment 24 to grasp a loop 29 tied in the line. By now pulling on the instrument, the drain member 12 can again be removed.

Figure 2:
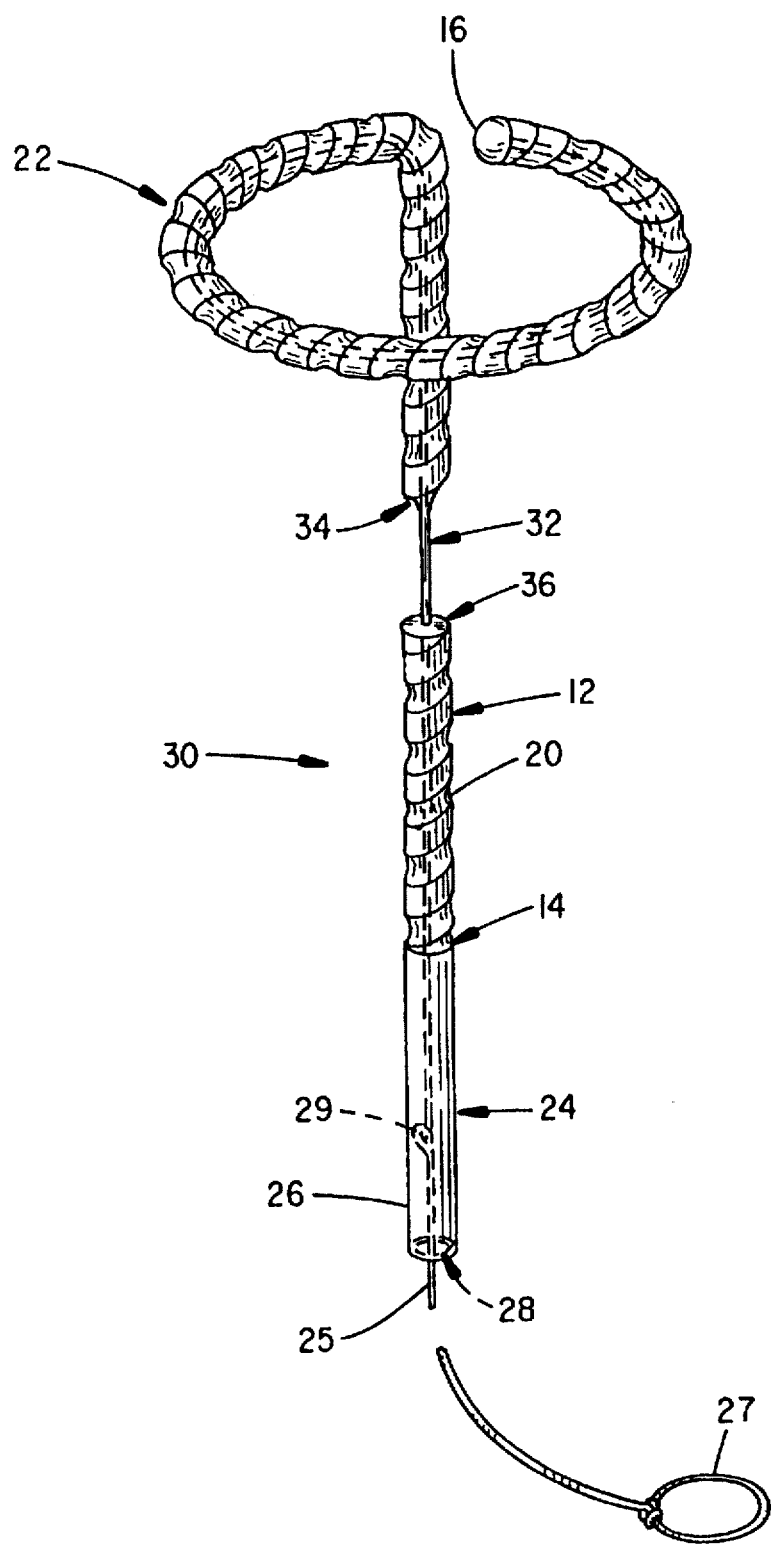
FIG. 2 is an elevational view of an alternative embodiment of the bladder drain in accordance with the invention.

An alternative embodiment of the invention is depicted in FIG. 2. The assembly of FIG. 2 is similar in most respects to the embodiment of FIG. 1 except that in the drain device 30 of FIG. 2, the tubular member 12 includes a narrowed and smooth, (non-channeled) segment 32 for cooperating with the external sphincter of the urethra. At the distal end of the segment 32 is a tapered shoulder 34 and at the proximal end is a more squared shoulder 36. The length of segment 32 is preferably in the range of from 0.5 cm to 5.0 cm and its outer diameter may be from 0.1 to 2.0 cm.

Figure 3:
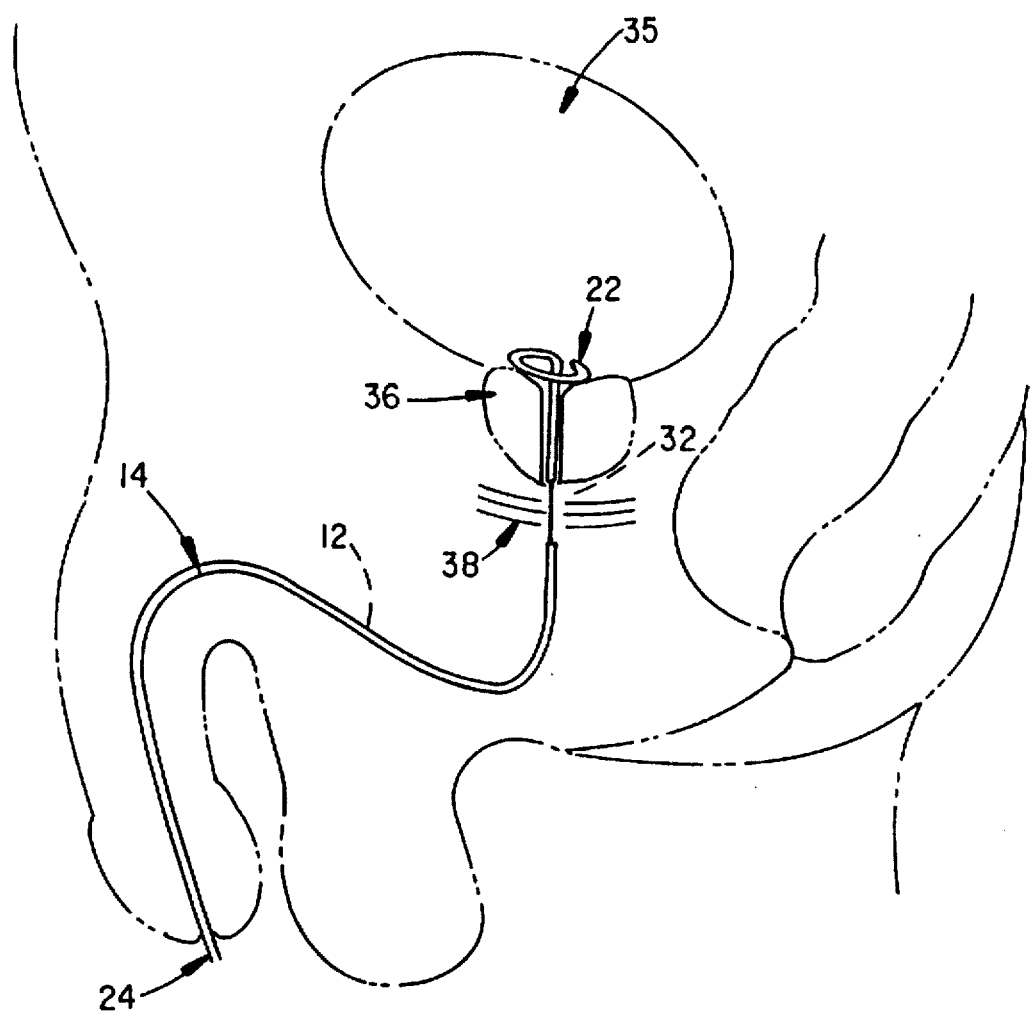
FIG. 3 is a view illustrating the embodiment of FIG. 2 inserted in the male urethra.

Referring next to FIG. 3, it shows the bladder drain device 30 of the embodiment of FIG. 2 disposed in the male urethra. The bladder retention portion 22 is located proximate the neck of the bladder 35 and with the installation stylet (not shown) fully removed, the bladder retention portion assumes its flat spiral configuration, thereby holding the drainage device in place. The portion of the drainage device 30 located above the tapered shoulder 34 is dimensioned to traverse the prostate 36 and with the zone 32 of reduced diameter extending through the external urethral sphincter 38. If desired, a string or monofilament 25 can be co-extruded with the drain device of FIG. 2 to inhibit stretching of the device in zone 32 when tensile forces are applied during removal of the drain.

The spiral curl 22 comprising the retention element is essentially perpendicular to the axial length of the drain and does not protrude appreciably above the base of the bladder. This low, flat profile distinguishes the present invention from the common Foley catheter, which is retained by means of a liquid filled balloon, as well as from the device shown in U.S. Pat. No. 4,738,667 to Galloway. The removal of a straightening stylet, as compared to the removal of an outer shield in the Galloway device, serves to minimize any irritation to the urethral wall of the patient. The use an internal straightening wire, as contrasted to a design utilizing an external straightening sleeve, also allows the existence of deeper drainage channels for a given outer diameter of the drain itself. While the bladder retention segment is depicted as a spiral or curl at the distal end of the body member 12 comprising the drain, it can be appreciated that an inflatable balloon adhered to the exterior of the tubular body 12 and communicating through a port bridged by the balloon leading to an inflation lumen may be employed to anchor the drain in a fashion similar to what is conventionally used with a Foley catheter. Such an arrangement is shown in FIGS. 1a, with the silastic balloon identified by numeral 39.

With the embodiment of FIG. 2 in place, as illustrated in FIG. 3, there will be a continuous flow of urine from the bladder 35 through the channel 20 formed in the exterior wall of the drain segment 30 with the channel emptying into the lumen of the urine collection tube 24. For patients having a functioning external urethral sphincter 38, the compressional force on the urethra in the zone 32 of the drain will close the urethra against that segment thereby blocking urine flow. When the patient desires to drain his or her bladder, he or she voluntarily relaxes the external urethral sphincter 38, allowing the contents of the bladder 35 to flow through the channel(s) formed in the wall surface of the drainage device 30 to again empty into the urine collection tube 24 leading to a collection bag not shown).

Figure 4:
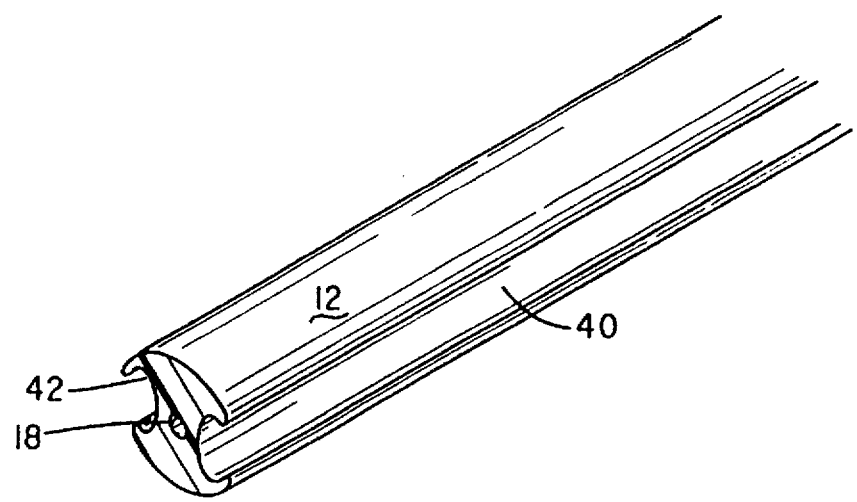
FIG. 4 is a fragmentary, enlarged perspective view of the portion of a bladder drain, illustrating two straight surface grooves.
Figure 5:
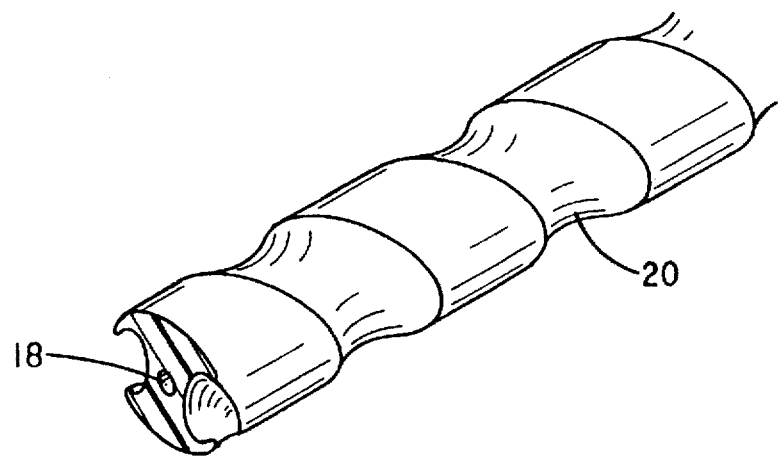
FIG. 5 is a fragmentary, enlarged perspective view of a portion of a bladder drain illustrating spiral surface grooves.

FIGS. 4 through 7 are included to show alternative ways of configuring the drainage segments 10 and 30 illustrated in FIGS. 1 and 2, respectively. In FIG. 4, the drainage segment 12 includes two straight longitudinal channels 40 and 42, diametrically opposed from one another, that extend substantially the entire length of the drainage segment. Also visible in FIGS. 4 through 7 is the stylet lumen 18. In the embodiment of FIG. 5, the surface grooves, as at 20, form a spiral, as in the embodiments of FIGS. 1 and 2. This spiral pattern may conveniently be formed during the fabrication process by twisting the segment 12 during the extrusion process prior to cooling. By controlling the amount of twisting, the pitch of the channels can be controlled.

While linear channels of the type shown in FIG. 4 may be provided in the drainage segment, a spiral channel configuration is preferred in that the lateral projections on the outer surface of the drain will interact with the urethral wall in such a fashion as to retard movement of the drain along the axial length of the urethra, thus minimizing undesired migration thereof. The side walls of the channels are preferably undercut or dished, as at 44 (FIG. 6), to thereby prevent irritation of the urethra, and to inhibit invagination of the urethral wall tissue into the channels.

Figure 6:
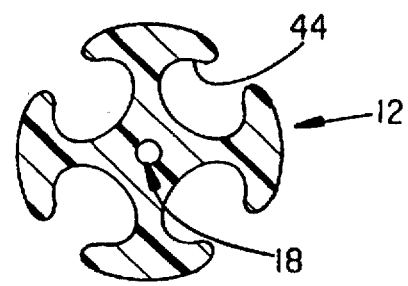
FIG. 6 is an enlarged cross-sectional view of a portion of the body of a bladder drain having four surface grooves extending the length thereof.
Figure 7:
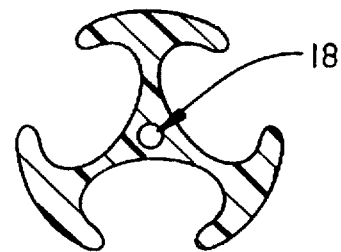
FIG. 7 is an enlarged cross-sectional view through a portion of the body of a bladder drain having three surface grooves extending along the length dimension thereof.

FIGS. 6 and 7, respectively, show cross-sectional views of the drain in which four and three channels, respectively, extend the length thereof.

Figure 8:
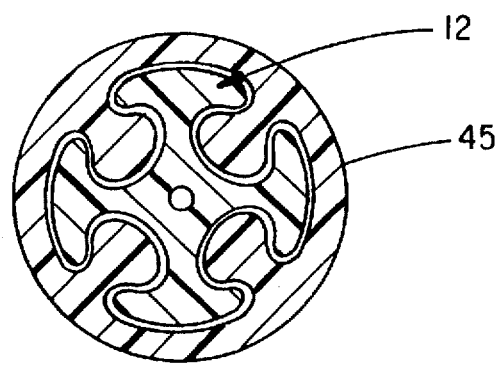
FIG. 8 is an enlarged cross-sectional view through a portion of the body of a bladder drain having a positionable smooth sleeve segment affixed thereto.

Referring to the cross-sectional view of FIG. 8, another way of forming a smooth segment along the length of the drainage member 12 for cooperating with the external urinary sphincter of a given patient is to provide a short length of tubing, as at 45, having an internal lumen whose side walls are complimentary in shape to the exterior surface of the grooved drainage member 12. Thus, the smooth portion of the tube 45 can be longitudinally adjusted to a location along the drain body where the urinary sphincter is located for that patient. Also, the outside diameter of the removable and replaceable smooth tubular segment 45 can be selected to accommodate the particular contractibility of the urinary sphincter of the patient to provide increased continence and will usually be in the range of from 0.3 cm to 1.0 cm.

It is further contemplated that the smooth tubular member 45 on the female urethral drain can comprise an inflatable sleeve surrounding the drain member 12 (FIG. 1). This is deemed to be beneficial in cases of female stress incontinence in that the sleeve can be inflated after placement to a degree effective to preclude leakage between the expandable sleeve and the neck of the bladder and to compensate for sphincter deficiency.

Figure 9:
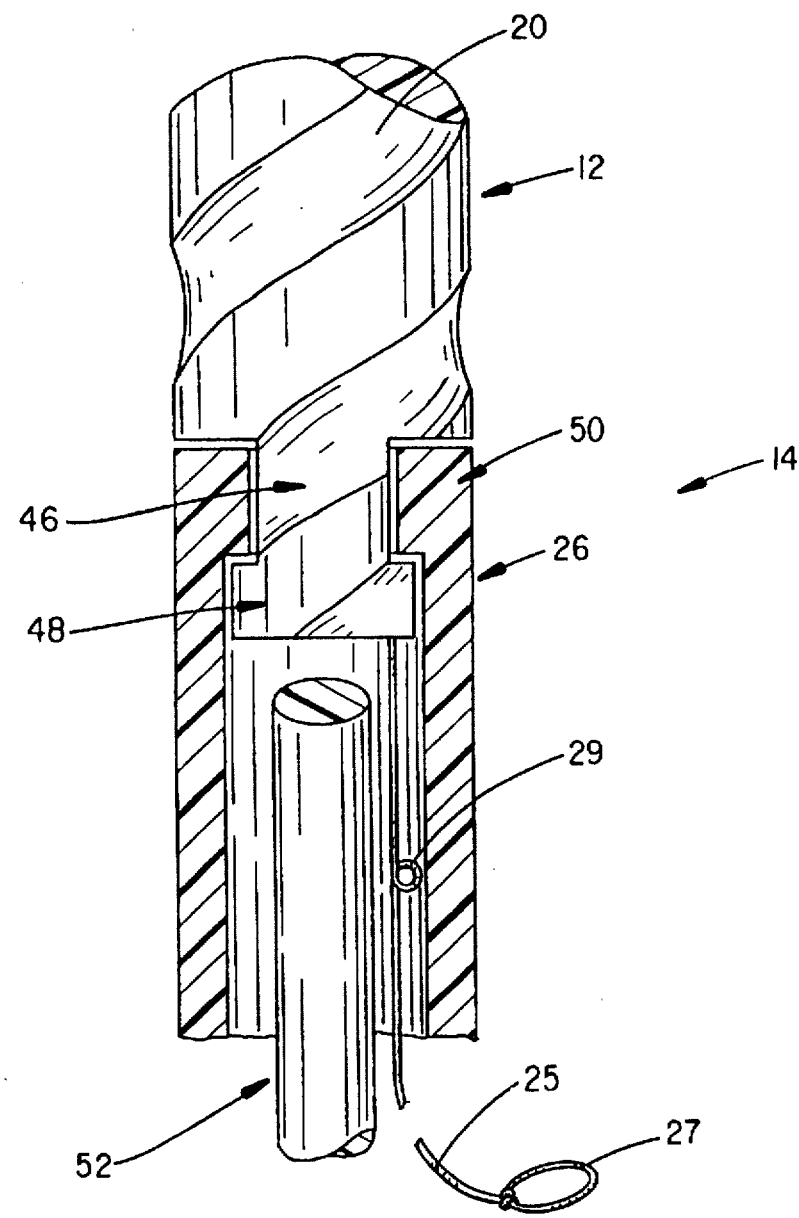
FIG. 9 is a partially sectional, fragmentary view of the embodiment of FIGS. 1 or 2 proximate the junction between the grooved bladder drain element and its associated collection segment.
Figure 9:
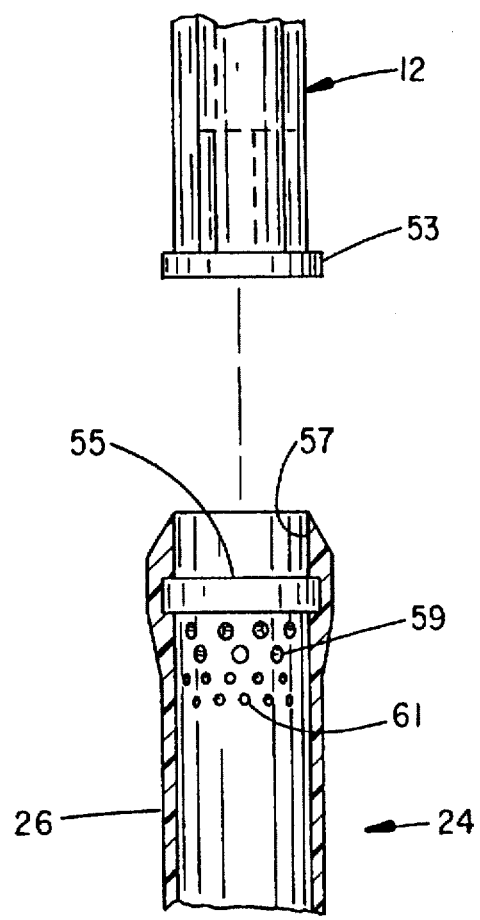

Referring now to FIG. 9, there is shown an enlarged fragmentary, partially sectioned view of the bladder drain showing the manner in which the fluid collection tube 24 is joined to the proximal end of the grooved drainage member 12. The proximal end 14 of the drainage member 12 is provided with a narrowed neck 46 which is followed by an expanded end portion 48. The fluid collection tube 26 has a complimentary profile 50 adapted to snap over the end portion 48 to occupy the narrowed neck 46. Urine passing along the channels 20 between the internal wall of the urethra and the drain is channeled into the lumen of the collection tube 26 to flow out its proximal end 28, either continuously when the embodiment of FIG. 1 is employed or in a controlled manner when the embodiment of FIGS. 2 or 8 is utilized. Detachment of the flexible plastic collection tube 26 may be accomplished by pulling on the tube 26 in the proximal direction while simultaneously employing a stabilizing push rod 52 to hold the drainage segment 12 in place. After detachment of the collection tube 26, the drain device is entirely contained within the urethral tract.

FIG. 9(a) is an enlarged, exploded, partial sectional view of a drain member 12 having straight (non-spiral) grooves such as is illustrated in FIG. 7 of the drawings and illustrating an alternative arrangement for connecting the drain body to an associated collection tube. The drain body 12 is molded or extruded so as to have a plurality of straight parallel grooves as best seen in FIG. 7. Surrounding the proximal end portion of the drain 12 is a ring member 53 which is secured to the exterior of the lobes of the drain body separated from one another by adjacent grooves. To better concentrate and direct the urine stream, the central portion of the drain body is cored out, leaving only the lobes depending in a zone of a predetermined length distal of the ring 53. The collection tube 24 includes an internal annular groove 55 into which the ring 53 on the drain body is adapted to be inserted. As such, the portion of the lobes on the drain body that are free from the central or core portion thereof fall within the lumen 57 of the collection tube and thereby directing the urine stream flowing down the longitudinal grooves in the drain body to flow into the lumen 57 of the collection tube.

To enhance the ability of the urine to find its way into the central lumen of the collection tube, it may be expedient to include a pattern of holes as at 59 through the wall of the collection tube where the size of the holes 59 are made slightly larger toward the distal end of the collection tube 24 and of a smaller size as at 61 at locations more proximal than the larger holes 51.

As those skilled in the art will appreciate from the foregoing description of the embodiment of FIG. 9, the same technique for detaching the plastic collection tube 26 from the drainage device 12 can be utilized with the embodiment of FIG. 9(a).

Figure 10:
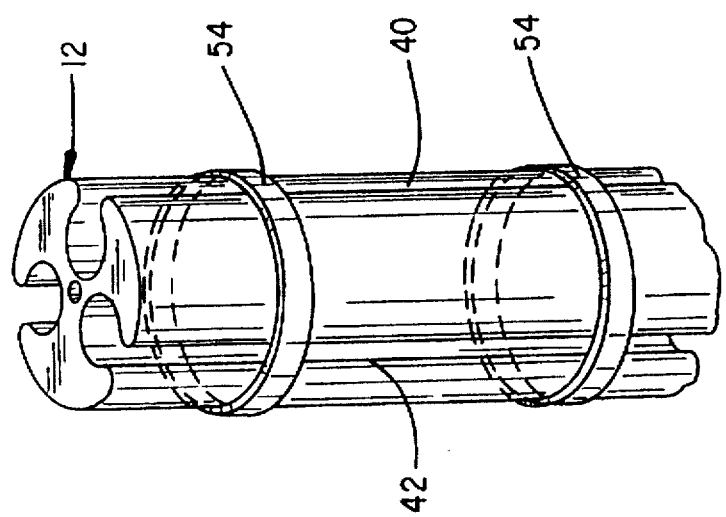
FIG. 10 is an enlarged, partial, perspective view of a segment of the drain of FIG. 7 and incorporating retention rings thereon.

To assist in preventing migration of the drain devices having linear channels as in FIGS. 4 through 7, a series of longitudinally spaced rings as at 54 in FIG. 10 may be placed about the drain body 12 at predetermined intervals. The rings are preferably relatively flat and are appropriately bonded to the drain body 12. It is found that the tissue of the inner wall of the urethra invaginates the channels 40, 42 on opposite sides of the rings 54, inhibiting longitudinal displacement of the drain assembly. With no limitation intended, the rings 54 may be approximately 2 mm wide and 1 mm thick. Further, they may be placed approximately 1 cm apart from one another along the length of the drain body 12 on one or both sides of any smooth segment of reduced diameter as at 32 in FIG. 2 that is intended to cooperate with the urinary sphincter. By providing rings 54 along the length of the drain device, it is no longer necessary to include a central styler receiving lumen 18. The styler, instead, can be routed up one of the surface channels 40 and 42 and will be constrained by the rings.

Figure 11:
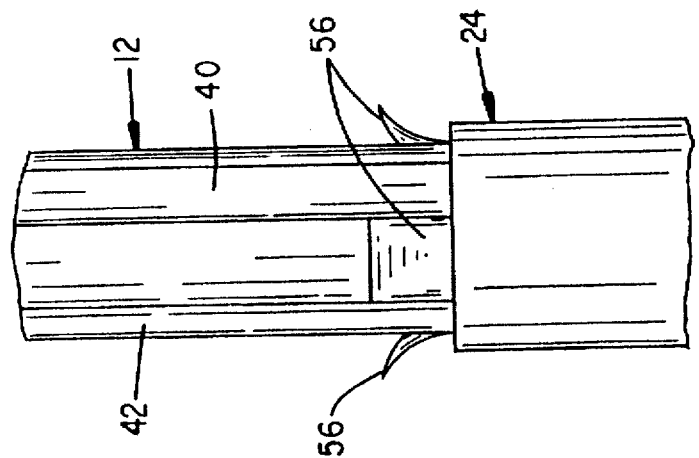
FIG. 11 is a partial side elevation of a drain device having the configuration of FIG. 7 and illustrating an alternative drain retention feature.

FIG. 11 shows an alternative anchoring arrangement to that shown in FIG. 10. Instead of incorporating spaced-apart rings extending about the drain body, small, laterally projecting tines 56 that are located proximate the junction between the drain body 12 and the collection tube 24'. The tines 56 are intended to engage the interior wall of the urethra to prevent migration of the drain assembly in the distal direction toward the urinary bladder. When it is desired to remove the drain, a force applied to the strand 25 (FIG. 1) will cause the tines 56 to deflect or collapse into alignment with the wall of the tubular body 12 and offer practically no drag or resistance against movement in the proximal direction. While the tines 56 are shown as being formed by cutting or slicing into the elastomeric material comprising the drain body 12, such tines can alternatively be provided on the collection tube 24'. Furthermore, rather than providing tines as at 56 in FIG. 11, the retention means can take the form of a bulbous protrusion (not shown) formed on the lobes of the drain body 12.

Figure 14:
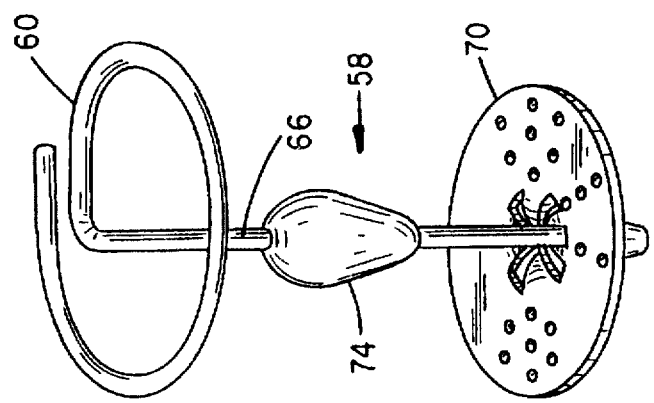
FIG. 14 illustrates the device of FIGS. 12 or 13 with a cuff member placed thereon when treating female stress incontinence.
Figure 13:
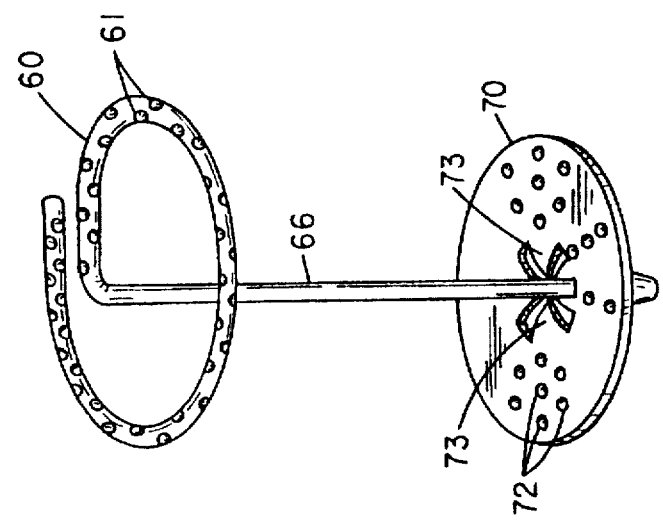
FIG. 13 illustrates the device of FIG. 12 but with an alternatively configured proximal retention means.
Figure 12:
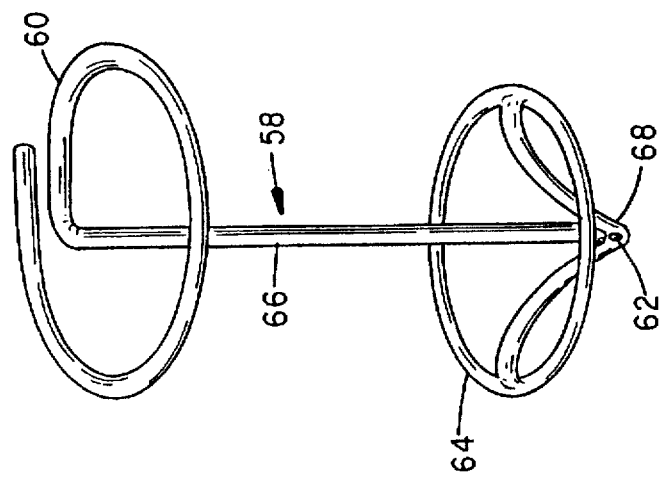
FIG. 12 illustrates an alternative embodiment of the invention for placement in the female urethra.

FIGS. 12 through 14 show the configuration of an alternative device insertable into the female urethra for addressing stress incontinence. It is seen to comprise an elongated, flexible, plastic rod which, in the instant embodiments, is free from surface channels throughout its length. Preformed at its upper end is a retention segment 60 which is intended for placement within the urinary bladder. Such placement is enhanced by inserting a suitable stylet through an aperture 62 for temporarily straightening the curl of the retention segment 60 and allowing its insertion into the urethral opening. When the device 58 has been advanced sufficiently far up the urethra such that the segment of the device forming the retention member 60 resides in the urinary bladder, upon removal of the stylet, the memory property of the plastic material comprising the device 58 allows the retention member to reform into a flat spiral shape as illustrated.

To prevent the upward migration of the device as it is being worn, it is also provided with a proximal retention segment 64 which, in FIG. 12, also comprises a flat ring-like segment that lies in a plane that is at a predetermined angle to the body portion 66 and that is dimensioned to abut the vestibule and underlie the labia minora. As such, the device may remain within the patient while still allowing normal sexual activity to take place.

Instead of forming the proximal end portion of the drain member 66 into a flat spiral such as is shown at 60 in FIG. 12, to create a retention member, it is also contemplated that a separate closed ring as at 64 positioned about the drain body and secured to it by connecting spokes made from a suitable soft plastic be used. This is the configuration illustrated in FIG. 12.

It has been found expedient to preform the device 58 so that the elongated straight segment 66 extends downward below the lower retention member 64 as indicated by numeral 68 in FIG. 12. Urine flow tends to follow the straight portion 66 due to surface tension effects and provides a proper urine stream leaving the urethra.

The embodiment of FIG. 13 is like that of FIG. 12 except that the proximal retention ring 64 of FIG. 12 is replaced by a highly flexible oval-shaped sheet of plastic 70 that is permeable to the flow of air, due to the fenestrated nature of the plastic material shown as a having a pattern of closely spaced openings, as at 72, extending through the thickness dimension thereof. Again, the air previous retention member disk 70 is sized and shaped to conform to the area of the body closely surrounding the urethral opening in the vestibule. The proximal end of the body member 66 extends below the retention member 70 and is supported by webs, as at 73, extending across a larger circular opening formed in the sheet 70 which permits urine to flow in a stream as it exits the device.

In the embodiment of FIG. 13, measures are taken to decrease the weight of the retention member 60. Here, the curl portion only is made tubular and is fenestrated by a plurality of openings 61 extending through the wall of the curl to the lumen thereof. This minimizes trauma to the bladder.

Referring next to FIG. 14, the incontinence control device 58 may include an appropriately sized cuff member 74 placed on and affixed to the straight shaft portion 66 of the device of FIGS. 12 and 13 at a location that will conform to the shape of the urethra proximate the woman's urinary sphincter. A urologist, fitting the woman with the device, will determine the appropriate size and shape of the cuff member 74 that will cooperate with the sphincter muscle to provide an effective seal when the sphincter is contracted. The cuff 74 may include a longitudinal bore sized so that the plastic rod 66 comprising the device and its retention member 60 can pass through that bore. Alternatively, the cuff member 74 may be provided with a fine slit extending through a side wall surface thereof to a central bore, allowing it to spreading the cuff me device 58 by first spreading the cuff member and fitting it over the straight segment 66. Releasing the cuff member allows it to close about the shaft 66.

Figure 15:
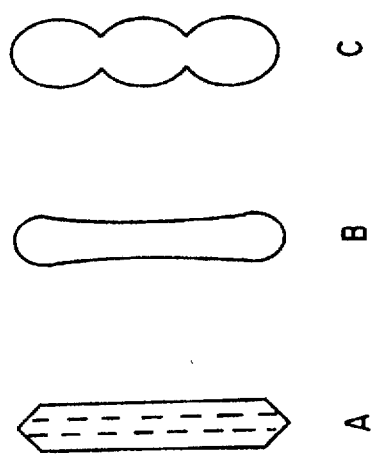
FIGS. 15a, b and c illustrate alternative shapes for the cuff member illustrated in FIG. 12.

FIGS. 15a, b and c illustrate alternative shapes for the cuff member 74 from which the urologist may choose in deciding which provides the best seal with the urethra when the urinary sphincter is contracted. The cuff of FIG. 15a is generally cylindrical but has conically tapered opposed ends to facilitate its being inserted and removed from the urethra along with the device 58. FIG. 15b is somewhat bone-shaped where the sphincter cooperates primarily with the narrowed zone between the two larger opposed end portions. The cuff of FIG. 15c has multiple annular narrowed regions which can assist deficient sphincter muscles to better coapt the urethral wall to the cuff during a sudden increase in bladder pressure occasioned by laughter, coughing or sneezing.

In any of the disclosed embodiments, it may prove efficacious to coat the drain member with hydrogel to render it more soft and lubricious to aid in insertion thereof. The coating may also incorporate a slow-release drug therein to combat urinary infection or to provide treatment to urinary organs.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A flexible, self-cleaning urethral drain for draining of urine and fluid from the bladder through the urethra of a patient comprising:

(a) a flexible, elongated drain body having a distal end and a proximal end with an outer diameter allowing passage through the urethra;

(b) bladder retention means located adjacent to the distal end of the drain body for retaining the drain body in place in the urethra;

(c) the drain body having an exterior surface with an open fluid drainage channel on said exterior surface cooperating with the wall of the urethra and of a sufficient depth for draining urine between the exterior surface of the drain body and the urethral wall; and (d) means on the drain body for inhibiting longitudinal migration of said drain body in a distal direction relative to the urethral wall.

2. The flexible, self-cleaning urethral drain as in claim 1 and further including a tubular collection segment affixed to the proximal end of the drain body, the tubular collection segment having an internal lumen in fluid communication with said at least one open fluid drainage channel for receiving urine from the at least one open fluid drainage channel of the drain body, the collection segment terminating at a proximal end external to the meatus.

3. The flexible, self-cleaning urethral drain as in claim 1 wherein the means for inhibiting longitudinal migration in a distal direction comprises a plurality of longitudinally spaced ring members disposed on the drain body and overlaying the open fluid drainage channel to define windows for tissue penetration.

4. The flexible, self-cleaning urethral drain as in claim 1 wherein the inhibiting means comprises a plurality of integrally formed tines extending laterally of the exterior surface.

5. The flexible, self-cleaning urethral drain as in claim 1 wherein the bladder retention means comprises an inflatable member.

6. The flexible, self-cleaning urethral drain as in claim 1 wherein the drain body comprises a flexible polymer material selected from the group consisting of silicone, silastic, polyurethane and polyethylene.

7. The flexible, self-cleaning urethral drain as in claim 6 wherein the polymer material has a durometer in the range of from 30 to 95 shore A.

8. A flexible, self-cleaning urethral drain as in claim 1 and further including a positionable sleeve member having a smooth exterior surface void of grooves and an interior surface conforming to the exterior surface of the drain body, including the at least one open fluid drainage channel.

9. The flexible, self-cleaning urethral drain as in claim 8 wherein the positionable sleeve member has a length between approximately 0.5 cm 5.0 cm.

10. The flexible, self-cleaning urethral drain as in claim 8 wherein the outer diameter of the positionable sleeve is in the range of from 0.3 cm and 2.0 cm.

11. The flexible, self-cleaning urethral drain ass in claim 1 and further including a positionable sleeve member having a smooth exterior surface void of grooves and an interior surface conforming to the exterior surface of the drain body.

12. The flexible, self-cleaning urethral drain as in claim 11 wherein said positionable sleeve member is generally cylindrical in shape.

13. The flexible, self-cleaning drain as in claim 11 wherein said positionable sleeve member is of non-uniform cross-section along the length thereof.

14. A flexible, self-cleaning urethral drain as in claim 1 wherein the drain body includes an integrally formed longitudinal segment of a predetermined diameter and located along the drain body to cooperate with the external urethral sphincter in the patient for providing continence when the sphincter is normally contracted, and allowing passage of urine along the at least one channel when the sphincter is relaxed.

15. The flexible, self-cleaning urethral drain as in claim 14 wherein the length of the longitudinal segment is between approximately 0.5 cm to 5.0 cm.

16. The flexible, self-cleaning urethral drain as in claim 14 wherein the outer diameter of the longitudinal segment is between approximately 0.1 to 1.0 cm.

17. A flexible, self-cleaning urethral drain as in claim 14 wherein a segment of the drain body proximal to the longitudinal segment joins to the longitudinal segment to form a squared shoulder.

18. The flexible, self-cleaning urethral drain as in claim 14 wherein the drain body tapers to the diameter of the longitudinal segment at a distal end of the longitudinal segment.

19. The flexible, self-cleaning urethral drain as in claim 18 wherein the at least one channel extends along at least a portion of said bladder retention means.

20. The flexible, self-cleaning urethral drain as in claim 1 wherein the bladder retention means comprises a curl at the distal end of the flexible drain body.

21. The flexible, self-cleaning urethral drain as in claim 20 wherein the curl has a flat profile and extends generally perpendicular to a longitudinal axis of the remainder of the drain body when installed in the bladder of the patient.

22. The flexible, self-cleaning urethral drain as in claim 20 wherein the tubular body includes a stylet receiving lumen and the curl is preformed and can be reversibly straightened by inserting a stiffening styler in the stylet-receiving lumen.

23. The flexible, self-cleaning urethral drain as in claim 20 wherein the means for inhibiting migration of the drain body toward the bladder is affixed to said drain body proximate said proximal end and adapted to cooperate with body tissue external to the urinary meatus.

24. The flexible, self-cleaning urethral drain as in claim 23 wherein the migration inhibiting means comprises a closed loop affixed to the drain body proximate the proximal end thereof.

25. The flexible, self-cleaning urethral drain in claim 23 wherein the bladder retention means comprises a curl at the distal end of the drain body and the migration preventing means comprise a flexible, elastomeric sheet of a predetermined shape configuration disposed proximate the proximal end of the drain body and conforming to the vestibule of a female patient without overlaying the vaginal opening and the clitoris of said female patient.

26. The flexible, self-cleaning urethral drain as in claim 25 wherein the said flexible elastomeric sheet is fenestrated to allow passage of air and other fluids therethrough.

27. A flexible, self-cleaning urethral drain for draining of urine and fluid from the bladder through the urethra of a patient comprising:

flexible, elongated drain body having a distal end and a proximal end with an outer diameter allowing passage through the urethra, said drain body including a curled segment proximate said distal end for retaining the drain body in place in the urethra, the drain body having an exterior surface adapted to cooperate with the wall of the urethra for draining urine and other fluids between the drain body and the urethral wall.

28. The flexible, self-cleaning urethral drain as in claim 27 wherein the curled segment comprises a tube having a wall defining a lumen and a plurality of openings formed through the wall and communicating with the lumen.

* * * * *